(12) United States Patent
Boccara et al.

(10) Patent No.: US 9,046,338 B2
(45) Date of Patent: Jun. 2, 2015

(54) FULL-FIELD OPTICAL COHERENCE TOMOGRAPHY SYSTEM FOR IMAGING AN OBJECT

(71) Applicant: LLTECH MANAGEMENT, Loos (FR)

(72) Inventors: Albert Boccara, Paris (FR); Anne Latrive, Paris (FR); Bertrand Le Conte De Poly, Paris (FR); Fabrice Harms, Orsay (FR)

(73) Assignee: LLTECH MANAGEMENT, Loos (FR)

( * ) Notice: Subject to any disclaimer, the term of this patent is extended or adjusted under 35 U.S.C. 154(b) by 0 days.

(21) Appl. No.: 13/846,378

(22) Filed: Mar. 18, 2013

(65) Prior Publication Data
US 2013/0235383 A1 Sep. 12, 2013

Related U.S. Application Data

(63) Continuation of application No. PCT/EP2011/066132, filed on Sep. 16, 2011.

(60) Provisional application No. 61/384,221, filed on Sep. 17, 2010.

(51) Int. Cl.
*G01B 9/02* (2006.01)
*A61B 5/00* (2006.01)
*G01N 21/47* (2006.01)

(52) U.S. Cl.
CPC .......... *G01B 9/02091* (2013.01); *A61B 5/0066* (2013.01); *A61B 5/0084* (2013.01); *G01N 21/4795* (2013.01)

(58) Field of Classification Search
CPC ............... A61B 5/0066; A61B 5/0084; G01B 9/02091; G01N 21/4795
USPC .................................................. 356/450–521
See application file for complete search history.

(56) References Cited

U.S. PATENT DOCUMENTS

| 4,533,247 A | * | 8/1985 | Epworth ...................... 356/479 |
| 2006/0146339 A1 | * | 7/2006 | Fujita ............................ 356/484 |
| 2007/0081166 A1 | * | 4/2007 | Brown et al. ................. 356/479 |
| 2007/0087445 A1 | | 4/2007 | Tearney et al. |

(Continued)

OTHER PUBLICATIONS

Arnaud Dubois, et al.; High-Resoultion Full-Field Optical Coherence Tomography With a Linnik Microscope—Applied Optics, Optical Society of America, Washington DC; US, vol. 41, No. 4, (Feb. 1, 2002), pp. 805-812, XP002373646, ISSN:0003-6935.

(Continued)

*Primary Examiner* — Tarifur Chowdhury
*Assistant Examiner* — Michael P Lapage
(74) *Attorney, Agent, or Firm* — Brinks Gilson & Lione (57) ABSTRACT

The present invention relates to a full-field optical coherence tomography system (300) for imaging an object (319), comprising a light source (301), a first interferometric device having means for splitting an input light beam and comprising at least a reflecting surface (307), a second interferometric device having means for splitting the spectrally modulated output beam and comprising at least a reflecting surface, a multichannel acquisition device (321), the system (300) being characterized in that at least one of the interferometric devices includes at least a focusing optical element arranged to focus at least one of the input beams or at least one of the output beams onto the corresponding reflecting surface of the corresponding interferometric device.

20 Claims, 4 Drawing Sheets

(56) References Cited

U.S. PATENT DOCUMENTS

| 2007/0229801 | A1 | 10/2007 | Tearney et al. | |
|---|---|---|---|---|
| 2008/0007733 | A1 | 1/2008 | Marks et al. | |
| 2010/0027020 | A1* | 2/2010 | Nebosis | 356/450 |
| 2010/0097616 | A1 | 4/2010 | Nebosis et al. | |
| 2012/0133946 | A1* | 5/2012 | Eckman et al. | 356/450 |

OTHER PUBLICATIONS

W.Y. Oh, et al.; Spectrally-Modified Full-Field Optical Coherence Microscopy for Ultrahigh-Risoution Endoscopic Imaging—Optics Express, OSA (Optical Society of America), Washington DC, US, vol. 14, No. 19, (Sep. 18, 2006), pp. 8675-8684, XP002441973; ISSN:1094-4087.

H.D. Ford et al; Fibre Imaging Bundles for Full-Field Optical Coherency Tomography—Measurement Science and Technology, IOP, Bristol, GB, vol. 18, No. 9, (Sep. 1, 2007), pp. 2949-2957, XP020118834; ISSN:0957-0233.

Weichao Wang et al.; Comparison of Different Focusing Systems for Common-Path Optical Coherence Tomography With Fiber-Optic Bundle as Endoscopic Probe—Optical Engineering, vol. 48, No. 10, (Oct. 2009), pp. 103001-1-103001-8, XP40506353, Bellingham, US.

* cited by examiner

*Fig. 1*

PRIOR ART

*Fig. 2*

PRIOR ART

FULL-FIELD OPTICAL COHERENCE TOMOGRAPHY SYSTEM FOR IMAGING AN OBJECT

CROSS-REFERENCE TO RELATED APPLICATIONS

This application is a continuation of International Application No. PCT/EP2011/066132 filed on Sep. 16, 2011, which claims the benefit of U.S. Provisional Application Ser. No. 61/384,221, filed on Sep. 17, 2010. The disclosures of the above applications are incorporated herein by reference.

FIELD

The present invention relates to a full-field optical coherence tomography system for imaging an object.

BACKGROUND

The statements in this section merely provide background information related to the present disclosure and may not constitute prior art.

The present invention is in the technical field of optical imaging. More particularly, the present invention is in the technical field of Optical Coherence Tomography. More particularly, the present invention is in the technical field of Full-Field Optical Coherence Tomography with a probe.

Optical Coherence Tomography (OCT) is an imaging technique based on low coherence interferometry (see for example J. G. Fujimoto et al., Optical biopsy and imaging using optical coherence tomography, Nature Medicine 1, 970-972 (1995)). Because of its good sectioning ability and a typical 10 micrometer-scale resolution it was found to be an efficient tool for in-depth imaging of biological tissues. In contrast with most of the available OCT approaches, e.g. time domain OCT or Fourier domain OCT, Full-Field OCT (FF-OCT) directly takes "en face" high resolution images (typically 1 µm, isotropic) using two-dimensional (2D) detectors, thus eliminating the need for lateral x y scanning (see for example A. Dubois et al., High-resolution full-field optical coherence tomography with a Linnik microscope, Applied Optics 41, 805-812 (2002)).

Figure 1:
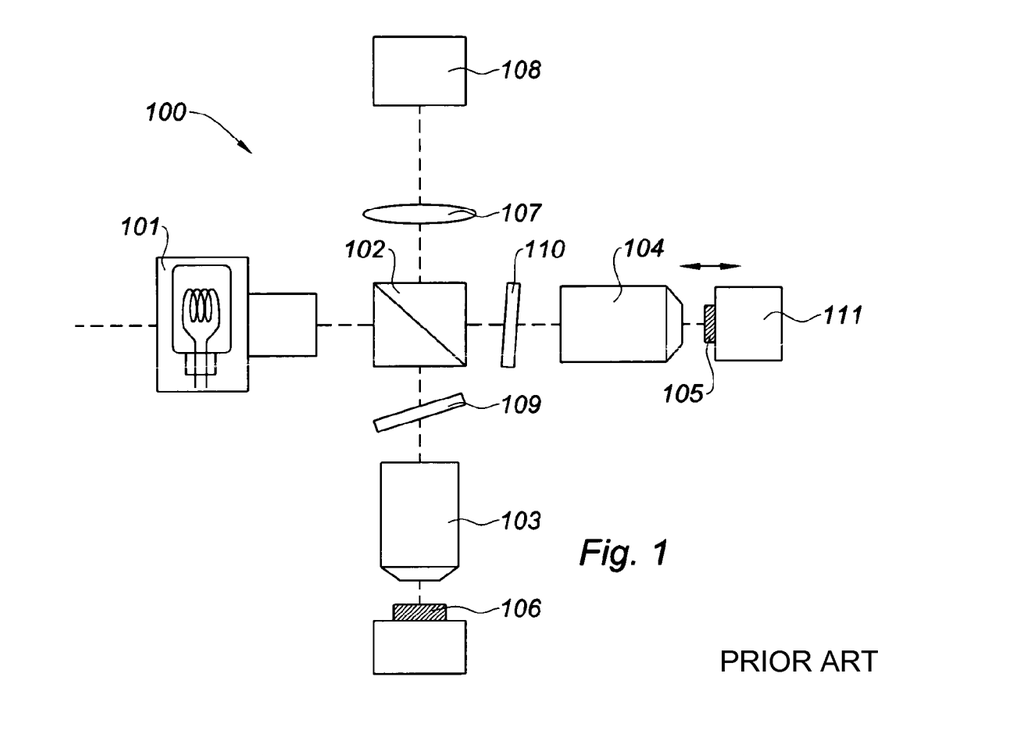
FIG. 1 shows a FF-OCT setup according to the prior art, previously described.

A typical FF-OCT setup with a Linnik interferometer and a modulation of the reference path using a piezoelectric (PZT) oscillator is represented on FIG. 1. It relies on the use of thermal sources or arcs or LEDs that are spatially incoherent, coupled to an interference microscope, for example a Michelson in the Linnik configuration as shown on FIG. 1. The FF-OCT system 100 comprises a source of partially coherent light 101, e.g. an halogen light source, a beam splitter 102, e.g. a non-polarizing beam splitter cube, defining two interferometric arms. For a Linnik configuration, both arms include a microscope objective of the same characteristics 103 and 104. In one arm a uniform reflective surface 105 is positioned at the focal plane of the objective and linked to an oscillator 111, allowing modulation of the optical path length of the reference arm, e.g. a piezo electric transducer. In the other arm the volume and scattering sample 106 is positioned at the focal plane of the objective 103. An adjustable dispersion balance system is included in both arms, e.g. rotating glass plates 109 and 110. A tube lens 107 is placed at the output of the interferometer in order to conjugate the focal planes of both objectives 103 and 104 with a multichannel detector 108.

All OCT systems have a limited maximum imaging depth in tissues of typically one to two millimeters due to absorption and scattering of light by the biological structures. For imaging of internal organs for example a probe is thus required.

Classical OCT, i.e. non Full-Field OCT, systems with probe are optical fibre versions of the Michelson interferometer, where 2D images are acquired with point-to-point scanning at the tip of the probe (see for example P. H. Tran et al., In vivo endoscopic optical coherence tomography by use of a rotational microelectromechanical system probe, Optics Letters 29, 1236-1238 (2004)). Such scanning systems require advanced miniaturized mechanical systems at the tip of the probe, as well as electric supply. The advantage of a FF-OCT setup is that it does not require any scanning since all images are taken "en face".

A FF-OCT system with probe has to address the problem of keeping the performances of FF-OCT in a set-up using a miniaturized, medically safe probe. The probe part cannot be directly integrated as an arm of the Linnik interferometer because its use would cause perturbations and damage the interference signal. Indeed if the probe comprises an optical fiber or fiber bundle, bends and twists in the fibers during in vivo measurements will create differences between the states of polarization of light in the reference and object arms, thus distorting the signal. Moreover it would also require to set identical probes in both arms of the Linnik interferometer, which would induce very large optical path lengths difficult to balance. On the contrary, in a system with two interferometers the probe is not part of an interferometer arm and is only used to transport an image. It is thus entirely passive and insensitive to its environment. Such a system is to privilege for in situ imaging, where one needs a system which is able to image outer or inner parts of the body that are difficult to reach. Thus FF-OCT systems with a probe use two coupled interferometers.

SUMMARY

Figure 2:
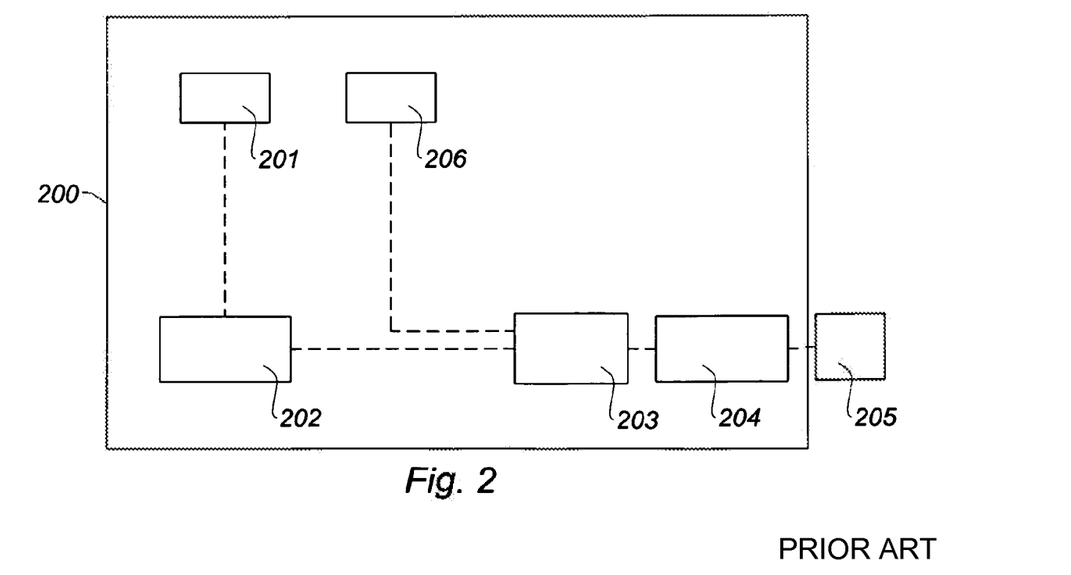
FIG. 2 is a block diagram of a FF-OCT system with probe according to the prior art, previously described.

The principle of the system is represented on FIG. 2. The system 200 comprises a light source 201, a first processing interferometer 202, a probe 203, a second distal interferometer 204 placed before the sample 205, a 2D detector 206. The light source 201 illuminates the processing interferometer 202, for example a Michelson interferometer. Light is injected into the probe 203, for example a fiber bundle, to the distal interferometer 204, for example a Linnik interferometer. Light coming back from the probe is directed to the 2D detector 206, for example a Charge-Coupled Device (CCD) or Complementary Metal Oxide Semiconductor (CMOS) camera, eventually using a beamsplitter.

Two FF-OCT set-ups with probe have already been proposed: a system using a Fizeau-configuration with a spatially coherent and temporally incoherent light source and an optical fibre bundle based probe (see H. D. ford et al., Fiber imaging bundles for full-field optical coherence tomography, Measurement Science and Technology 18, 2949-2957 (2007)); and a system using a spatially and temporally incoherent light source, a processing Michelson interferometer, a distal Linnik interferometer at the end of an optic fiber, and a fiber bundle for 2D image collection (see W. Y. Oh et al., Spectrally-modulated full-field optical coherence microscopy for ultrahigh-resolution endoscopic imaging, Optics Express 14, 8675-8684 (2006)).

The first system uses a simple miniaturized probe suitable for endoscopy but demonstrates a low Signal-to-Noise-Ratio (SNR) performance, typically 36 dB, which does not allow for biological imaging.

The second system demonstrates its ability to image biological samples but the use of a complete Linnik interferometer or other imaging interferometers at the distal end of the probe does not allow in vivo endoscopic imaging mainly because of its size.

Therefore no FF-OCT set-up with probe suitable for in vivo biomedical endoscopic imaging has already been demonstrated.

To summarize the problems risen by the already proposed FF-OCT setups:

using a spatially coherent light source such as a pulsed laser or a super-luminescent diode makes it possible to illuminate the sample interferometer with large optical path length differences but induces crosstalk that limits the sensitivity (see H. D. ford et al., Fibre imaging bundles for full-field optical coherence tomography, Measurement Science and Technology 18, 2949-2957 (2007));

using a spatially incoherent light source and a Michelson type interferometer to process the illuminating beam is possible but using a distal interferometer like a Linnik or a Michelson or a Mirau is not compatible with the size requirements for an endoscope.

The present invention aims at overcoming the aforementioned problems and relates to a full-field optical coherence tomography system for imaging an object, comprising:

a light source generating an input light beam having a low temporal coherence, a first interferometric device having:

means for splitting the input light beam into a first input beam and a second input beam, the first input beam and the second input beam being recombined into a spectrally modulated output beam, at least a reflecting surface arranged to reflect the first input beam or the second input beam, a second interferometric having:

means for splitting the spectrally modulated output beam into a first output beam and a second output beam, at least a reflecting surface arranged to reflect the first output beam or the second output beam, a multichannel acquisition device arranged to receive a recombination of the first output beam and the second output beam, the system being characterized in that at least one of the interferometric devices includes at least a focusing optical element arranged to focus at least one of the input beams or at least one of the output beams onto the corresponding reflecting surface of the corresponding interferometer device.

Then, in a system according to the invention, the presence of such a focusing optical element in at least one of the interferometric devices makes it possible to have a large optical path length difference between the first input beam and the second input beam, or between the first output beam and the second output beam, for example typically over 1 mm, while keeping the spectral modulation level of the spectrally modulated output beam.

Indeed, at short path length differences, typically inferior or equal to 0.5 mm, the spectrally modulated output beam suffers from the damaging effects of a superimposed parasitic signal. The parasitic signal appears in the corresponding interferometric device because of spectral inhomogeneities within the field of view, as explained later on.

In Full Field OCT, all pixels within the field of view, which we called the x y plane, are recorded simultaneously. If we consider the corresponding interferometric device, at one pixel x0 y0 corresponds one optical path length difference created by the first interferometric device, which we call d0. In an ideal set-up, all pixels should have the same optical path length difference called d. However, the beamsplitter used in the interferometric device actually does not have a perfectly plane surface: the best beamsplitters industrially available have a roughness around a tenth of the wavelength. It implies that each pixel x0 y0 has an optical path length difference d0 which differs from the optical path length differences of the other pixels by typically one tenth to one half of the wavelength. Thus, in the whole field of view, it results in a distribution of distinct optical path length differences di, with a given d as statistical mean and a typical deviation between one tenth and one half of the wavelength. Now in fact the optical path length difference d0 created at one pixel x0 y0 determines the frequency f0 of the interference fringes which modulate the light source spectrum. f0 increases with d0. In consequence, in the whole field of view the distribution of optical path length differences di is equivalent to a distribution of spectral modulation frequencies fi, so that the field of view can be described as spectrally inhomogeneous.

These optical spectral inhomogeneities created in the interferometric device are localized at infinity. However, in an optical set-up with a photodetector forming a multichannel acquisition device, one is bound to use at least one focusing optic, for example in order to focus light onto the photodetector. Thus the spectral inhomogeneities are localized in the back focal plane of the focusing optic. For example if one uses a microscope objective to inject light into the interferometric device, the spectral inhomogeneities are localized inside the pupil of the microscope objective. Since it is not experimentally possible to achieve a perfect conjugation, the inhomogeneities are then projected onto the photodetector and contribute to the image.

In Full Field OCT, the interferometric signal (i.e. the spectrally modulated output beam) is extracted from the background using a phase-shifting method, typically with an oscillator such as a piezo electric transducer. The piezo electric transducer can modulate the optical path length difference. At least two images are recorded successively, the second image called "out-of-phase" having a phase shifted by pi compared to the first image called "in-phase". By subtracting the two images, one can substantially eliminate the background and keep only the interferometric signal.

In a system according to the invention, the in-phase image and the out-of-phase image do not have the same optical intensity I, which is integrated by the multichannel acquisition device over the whole wavelength range. This is due to different factors:

the temporal fluctuations of the light source between the successive recordings of the images, and the fact that the light source experimental spectrum shape is not perfectly smooth.

Figure 3:
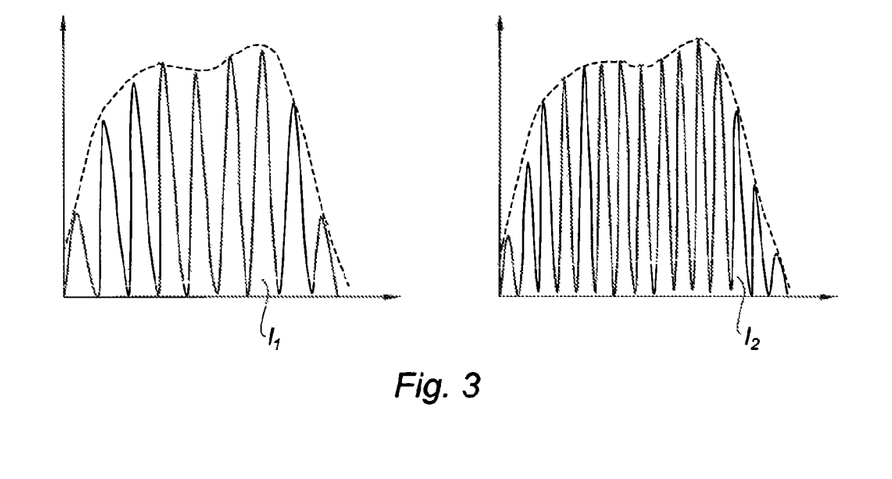
FIG. 3 shows examples of a spectrally modulated output beam, previously described, wavelength (arbitrary units) in abscissa and intensity (arbitrary units) in ordinate.

Indeed, each image has a different mean optical path length difference, and so a different mean spectral modulation frequency called f1 and f2. As shown on FIG. 3, the spectrally modulated output beam of the interferometric device is a product of the interference fringes, determined by the spectral modulation frequency f1 or f2, with the envelope of the source spectrum. Different spectral modulation frequencies will induce different convolution results, and thus different intensities I1 and I2 integrated over the wavelength range. As a consequence, the subtraction of the in-phase image and the out-of-phase image is a subtraction of two images with two backgrounds of different intensities, so that the phase-shifting subtraction method is not efficient to substantially eliminate the background and extract the interferometric signal. However if the field of view were spectrally homogeneous, that is if one image could be characterized by only one frequency f instead of a distribution of frequencies fi for each pixel, one could quite easily perform a normalization of each image so as to achieve the same mean intensity I. In this case, the phase-shifting subtraction method would be efficient. But since each pixel in the image has a different fi, each pixel also has a different mean intensity Ii. It is not possible in this condition to perform a renormalization. When the two images are subtracted, it results in a residual "ghost" image which corresponds to the distribution of optical frequencies within the field of view.

In order to eliminate this ghost image, it was found that the best solution is to increase the optical frequencies fi, which is equivalent to increase the optical path length difference di. Thus the differences between the mean intensities Ii decrease until the point where the ghost image has the same level as the residual shot noise and is thus not visible. The limit D where this happens depends on the light source spectrum. Experimentally, it was found that this happens for optical path length differences di substantially superior or equal to 1 mm. In consequence, we need an interferometric device able to produce an output beam with a mean path length difference substantially superior or equal to 1 mm, using spatially and temporally incoherent light for the aforementioned explained reasons.

Figure 4:
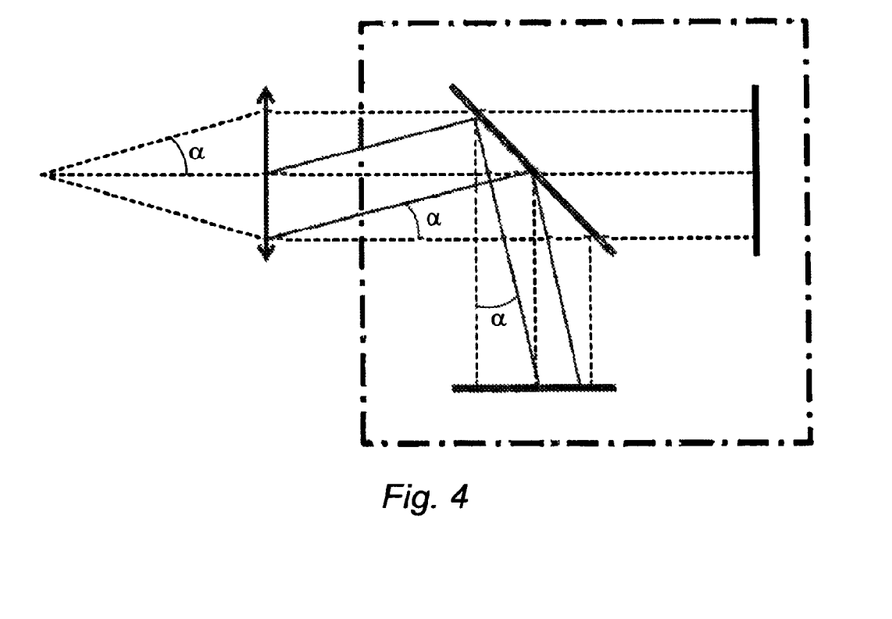
FIG. 4 shows a distribution of different angles for light within the field of view in a Michelson interferometer, previously described.

Compared to the state of the art, the system according to the invention allows large path length differences, typically superior or equal to about 1 mm, while keeping the spectral modulation level. Indeed a Michelson type interferometer, comprising a beamsplitter and two reflective surfaces, such as those used in the prior art, cannot be used at large path length differences with spatially incoherent light. Since light is injected with different angles of propagation, light in the Michelson interferometer also propagates at different angles, depending on the characteristics of the optical elements used for injection into the interferometer, as shown on FIG. 4. The distribution of different angles within the field of view creates a distribution of different optical path lengths. If the maximal path length difference between two rays of spatially incoherent light exceeds a fraction of the wavelength, for example typically a quarter of the wavelength, the spectral modulation level is significantly reduced. This is why it is not possible to achieve large mean path length differences without reducing the efficiency of the system.

However, using at least one focusing optical element in at least one arm of the interferometric device arranged to focus at least one beam onto at least one reflecting surface makes it possible to reduce this distribution of optical path lengths. Thus optical path length differences typically superior or equal to about 1 mm were achieved.

So, a system according to the invention is especially suitable in the technical field of Full Field OCT with a probe, particularly a miniaturized probe, said probe being intended to be coupled to the first interferometric device or the second interferometric device. Indeed, it is henceforth possible to use light having a low spatially coherence, which reduces crosstalk that limits sensitivity.

According to an embodiment of the invention, the first interferometric device has a first arm and a second arm respectively comprising a first reflecting surface and a second reflecting surface respectively arranged to reflect the first output beam and the second output beam, and the first interferometric device includes at least a focusing optical element in said first arm or in said second arm respectively arranged to focus the first output beam onto said first reflecting surface or the second output beam onto said second reflecting surface.

In an implementation of the invention, the focusing optical element comprises objective optics, such as microscope optics, so that the first interferometric device forms a Linnik interferometer.

In an advantageous way, the first interferometric device and the second interferometric device each comprise at least a lens, preferably a graded refractive index lens, the lens of the first interferometric device and the lens of the second interferometric device having the same optical characteristics.

Then, it is possible to compensate the large path length difference between the first input beam and the second input beam, and to compensate the dispersion. Moreover, such lenses are passive optical components which can be easily implemented on a probe, particularly a miniaturized probe. Consequently, this is suitable for in vivo imaging.

According to an embodiment of the invention, the second interferometric device has a first arm and a second arm respectively comprising a first reflecting surface and a second reflecting surface respectively arranged to reflect the first output beam and the second output beam, and the second interferometric device includes at least a focusing optical element in said first arm or in said second arm respectively arranged to focus the first output beam onto said first reflecting surface or the second output beam onto said second reflecting surface.

In an advantageous way, the focusing optical element of the second interferometric device is designed to introduce an optical path length difference between the first output beam and the second output beam substantially equal to the optical path length difference between the first input beam and the second input beam.

Then, the optical path length difference of the second interferometric device is substantially matched to the optical path length difference of the first interferometric device so that an optical section of the object can be obtained.

In an implementation of the invention, the focusing optical element of the second interferometric device comprises objective optics, such as microscope optics, so that the second interferometric device forms a Linnik interferometer.

According to an embodiment of the invention, the first interferometric device or the second interferometric device is a lens-based interferometer comprising at least two lenses, preferably graded refractive index lenses, said two lenses being arranged to form an optical cavity.

According to an embodiment of the invention, the system further comprises a probe, preferably a miniaturized probe, coupled to the first interferometric device or the second interferometric device, said probe having an end called distal end intended to be oriented toward the object.

Then, such a system is especially suitable for in vivo imaging.

In an implementation of the invention, the lens of the first interferometric device or of the second interferometric device is positioned at the distal end of the probe.

In a variant, the lens of the second interferometric device is positioned toward the multichannel acquisition device.

According to an embodiment of the invention, the first interferometric device or the second interferometric device presents a common optical path within the probe.

Then, such a first interferometric device or such a second interferometric device particularly avoids the dispersion of light and different states of polarization of light respectively between the first input beam and the second beam or between the first output beam and the second output beam.

According to an implementation, the probe is a miniaturized probe comprising a fiber bundle having a diameter between about 0.2 mm and about 10 mm, preferably between about 0.2 mm and about 5 mm, more preferably substantially equal to 1 mm.

Then, such a miniaturized probe is simple and easy to build because it has no moving parts and only a few passive optical components. It is medically safe and unlike systems according to the prior art it can achieve a very small diameter, typically 1 mm, which does not depend on any distal mechanics.

In a variant, the probe is a miniaturized probe comprising a plurality of optical lenses, preferably graded refractive index lenses, each optical lens having a diameter between about 0.5 mm and about 5 mm, preferably between 1 mm and about 3 mm, more preferably substantially equal to 2 mm.

Then, such a miniaturized probe is simple and easy to build because it has no moving parts and only a few passive optical components. It is medically safe and unlike systems according to the prior art it can achieve a very small diameter, typically 2 mm, which does not depend on any distal mechanics.

According to an implementation, the optical path length difference between the first input beam and the second beam, or between the first output beam and the second beam, is superior or equal to about 1 mm.

According to an embodiment of the invention, the first interferometric device and the second interferometric device comprise polarizing optics.

Then, such polarizing optics suppresses the residual incoherent signal made by parasitic light.

According to an embodiment of the invention, the system further comprises at least a motorized component, such as a linear stage or an actuator, the motorized component being designed to control the optical path length difference between the first input beam and the second input beam, or between the first output beam and the second output beam.

Then, it is possible to reconstruct a spatial 3D image of the object.

According to an implementation, the motorized component is arranged in the first interferometric device or in the second interferometric device.

In a variant, the motorized component is arranged on the probe.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 5:
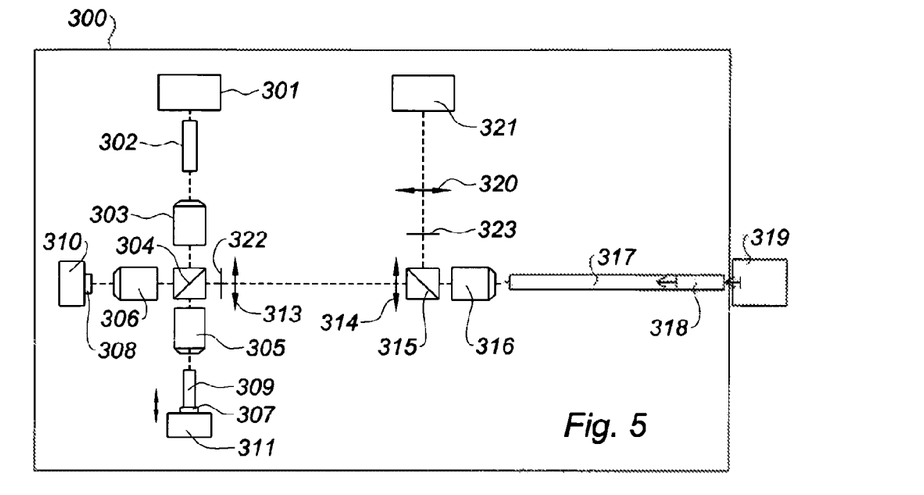
FIG. 5 shows an experimental set-up according to a first embodiment of a FF-OCT system with probe according to the invention.

FIG. 5 shows one embodiment of a FF-OCT system according to the invention.

The system 300 comprises a light source 301 generating an input light beam having a low temporal coherence. The light source 301 is spatially and temporally incoherent in order to reduce crosstalk and consequently increase the SNR. It can be for example a Xenon arc lamp.

Moreover, the system 300 comprises a first interferometric device, called processing interferometer. The emitted light is transported to the processing interferometer using for example an optical fiber 302 and a microscope objective 303 for reinjection into the processing interferometer.

The processing interferometer has a beam splitter 304 forming means for splitting the input light beam into a first input beam and a second input beam, the first input beam and the second input beam being recombined into a spectrally modulated output beam. The beam splitter 304 is for example a non-polarizing beam splitter cube with anti-reflection coating.

The processing interferometer has a first arm and a second arm respectively comprising a mirror 307 forming a first reflecting surface and a mirror 308 forming a second reflecting surface respectively arranged to reflect the first input beam and the second input beam. The two mirrors 307, 308 have the same optical characteristics.

The processing interferometer includes two microscope objectives 305, 306 with the same optical characteristics so that the processing interferometer is a Linnik interferometer. Each microscope objective 305, 306 forms a focusing optical element in the corresponding arm of the processing interferometer arranged to focus the corresponding input beam onto the corresponding reflecting surface.

Moreover, the processing interferometer comprises a gradient index-type (GRIN) lens 309 with pitch=0.5*n, n being a positive integer, typically pitch=0.5 or 1, attached to the mirror 307 in the first arm.

Moreover, the system 300 comprises a first motorized component 310, such as a linear stage or an actuator, designed to control the optical path length difference between the first input beam and the second output beam. More precisely, the first motorized component 310 is used for path length difference scanning, i.e. in-depth scanning of the object allowing 3D imaging. The system 300 comprises a second motorized component 311, such as a PZT actuator, which is used both for path length modulation and fine path length difference adjustments between the first arm and the second arm.

Moreover, the system 300 comprises a second interferometric device, called imaging interferometer, comprising a second GRIN lens 318.

Moreover, the system 300 comprises a probe 317, more precisely a miniaturized probe, having an end called distal end intended to be oriented toward the object 319. The probe 317 is coupled to the imaging interferometer.

Moreover, the system 300 comprises a 2D detector 321 forming a multichannel acquisition device.

The GRIN lens 309 in the first arm of the processing interferometer induces a path length difference in glass which is compensated by the second GRIN lens 318 with same optical characteristics placed at the distal end of the probe 317. Of course, the path length difference could be compensated by one or several lens(es).

Light from the processing interferometer is injected into the probe 317 using for example a microscope objective 316. An optical system, for example an afocal system, comprising for example two lenses 313 and 314 of same focal length, can be used to conjugate the pupil of this microscope objective 316 with the pupil of the first microscope objective 303.

The probe 317 can comprise a flexible fiber bundle, for example a bundle of 30 000 fibers for a diameter of 0.9 mm but other diameters ranging from 0.2 mm to a few mm are available and the number of fibers could be as large as 10 0000 (see for example Sumitomo IGN-08/30 or Fujikura FIGH-100-1500N). One or several lens(es), for example a GRIN lens 318 with same characteristics as the GRIN lens 309 used in one arm of the processing interferometer is used to compensate for the large path length difference of the processing interferometer and for dispersion, it can be attached to the fiber bundle using for example glue. The reflectivity of the bond between the fiber bundle and the GRIN lens 318 or the reflectivity of the surface of the fiber bundle, which constitutes the reference of the distal interferometer, can be adjusted in order to adjust the SNR of the set-up. The probe is placed in the proximity of the object 319.

A beam splitter 315, for example a pellicle beam splitter, reflects light coming back from the probe 317 through a focusing lens 320 onto the 2D detector 321, for example a CCD or CMOS camera. Parasitic light back-reflected from optical elements constitutes a residual incoherent signal which reduces the SNR, and in order to suppress this signal polarization can be used. A first polarizer 322 is inserted after the processing interferometer, and a second polarizer 323 rotated by 90 degrees in comparison with the first polarizer 322 is inserted before the detector 321. A polarizing beam splitter cube can also be used instead of two polarizers and a beam splitter. Fiber bundles do not conserve polarization states of light, so that light coming back from the fiber bundle is depolarized and can arrive through the polarizer 323 onto the detector 321, whereas parasitic light is stopped by the polarizer 323.

Figure 7:
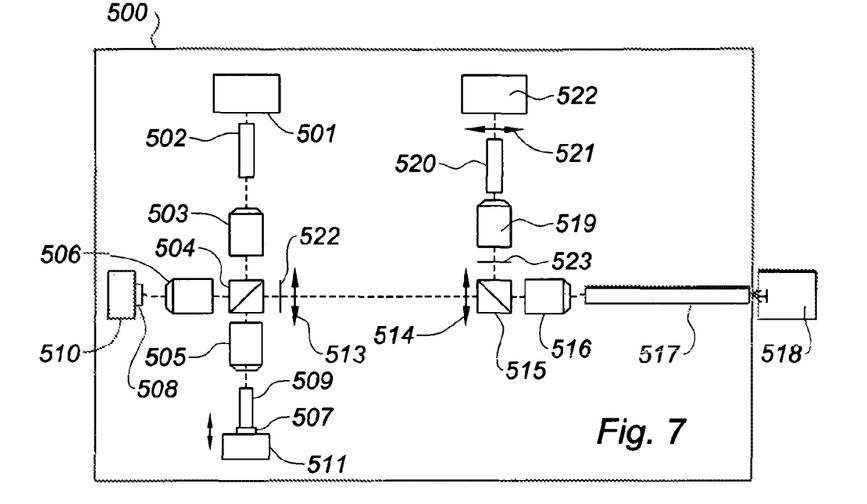
FIG. 7 shows an experimental set-up according to a third embodiment of a FF-OCT system with probe according to the invention.

The embodiment shown in FIG. 7 differs from the embodiment shown in FIG. 5 in that the GRIN lens 520 is placed before the 2D detector 522.

FIG. 7 shows one embodiment of a FF-OCT set-up according to the invention, using a first Linnik interferometer, a fiber bundle based probe, a second lens based interferometer placed after the probe.

The FF-OCT set-up 500 comprises a light source 501, a Linnik interferometer, a beamsplitter 515, a fiber bundle based probe 517, a 2D detector 521.

The light source 501 is spatially and temporally incoherent in order to reduce crosstalks and consequently increase the SNR. It can be for example a Xenon arc lamp. The emitted light is transported to the processing interferometer using for example an optical fiber 502 and a microscope objective 503 for reinjection into the first interferometer.

The first Linnik interferometer comprises a beamsplitter 504, for example a non-polarizing beamsplitter cube with anti-reflection coating, two microscope objectives with the same optical characteristics 505 and 506, two mirrors with the same optical characteristics 507 and 508, a GRIN lens 509 with pitch=0.5*n, n being a positive integer, for example pitch=1, attached to one mirror in one arm, a motorized linear stage or actuator 510 for path length difference scanning allowing 3D imaging, and a PZT actuator 511 used both for path length modulation and fine path length difference adjustments between the two arms. The GRIN lens 509 in one arm of the Linnik interferometer induces a path length difference in glass which is compensated by one or several lens(es), for example a second GRIN lens 520 with same optical characteristics placed before the detector.

Light from the first interferometer is injected into the probe using for example a microscope objective 516. An optical system, for example an afocal system, comprising for example two lenses 513 and 514 of same focal length, can be used to conjugate the pupil of this microscope objective 516 with the pupil of the first microscope objective 503.

The probe can comprise a flexible fiber bundle 517, for example a bundle of 30 000 fibers for a diameter of 0.9 mm but other diameters ranging from 0.2 mm to a few mm are available and the number of fibers could be as large as 10 0000 (see for example Sumitomo IGN-08/30 or Fujikura FIGH-100-1500N). The probe is placed in the proximity of the sample 518.

A beamsplitter 515, for example a pellicle beamsplitter, reflects light coming back from the probe through a focusing lens 519, for example a microscope objective, onto the second interferometer. The second interferometer comprises one or several lens(es), for example a GRIN lens 520 with same characteristics as the GRIN lens 509 used in one arm of the processing Linnik interferometer is used to compensate for the large path length difference of the first interferometer and for dispersion.

A focusing lens 521 focuses light on the 2D detector 521, for example a CCD or CMOS camera. Parasitic light back-reflected from optical elements constitutes a residual incoherent signal which reduces the SNR, and in order to suppress this signal polarization can be used. A first polarizer 522 is inserted after the first interferometer, and a second polarizer 523 rotated by 90 degrees in comparison with the first polarizer 522 is inserted before the detector 521. A polarizing beamsplitter cube can also be used instead of two polarizers and a beamsplitter. Fiber bundles do not conserve polarization states of light, so that light coming back from the fiber bundle 517 is depolarized and can arrive through the polarizer 523 onto the detector 521, whereas parasitic light is stopped by the polarizer 523.

Figure 6:
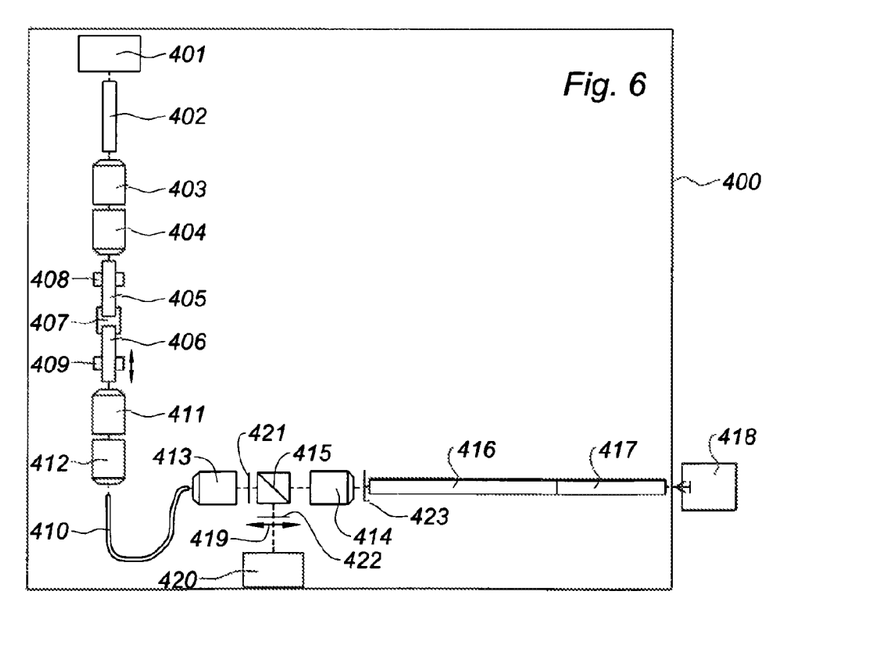
FIG. 6 shows an experimental set-up according to a second embodiment of a FF-OCT system with probe according to the invention.

The embodiment shown in FIG. 6 differs from the embodiment shown in FIG. 5 in that the processing interferometer is a lens-based interferometer.

FIG. 6 shows a second embodiment of a FF-OCT set-up with probe according to the invention, using a lens based processing interferometer and a lens based probe.

It comprises a light source 401, a lens based interferometer, a beam splitter 415, a lens based probe 416 with one or several lens(es) 417 attached, a 2D detector.

The light source 401 is spatially and temporally incoherent in order to reduce crosstalk and consequently increase SNR. It can be for example a Xenon arc lamp. The emitted light is transported to the processing interferometer using for example an optical fiber 402 and two microscope objectives 403 and 404 for reinjection into the processing interferometer.

The lens based processing interferometer comprises at least two lenses forming an optical cavity. It can comprise for example two GRIN lenses 405 and 406 with pitch=0.25+ 0.5*n, n being a positive integer, typically pitch=0.25, and an index-matching medium 407 in-between, for example oil or gel, a motorized linear stage or actuator 408 for path length difference scanning, i.e. in-depth scanning of the sample allowing 3D imaging, and a PZT tube actuator 409 used both for path length modulation and fine path length difference adjustments. The optical cavity of the lens based processing interferometer is not necessarily made of GRIN lenses, it can be for example two microscope objectives and two partially reflective surfaces.

Light from the processing interferometer is injected into an optical fiber bundle 410 using for example two microscope objectives 411 and 412. The optical fiber bundle delivers light into the probe using two microscope objectives 413 and 414.

The probe comprises one or several lens(es), for example a GRIN relay lens 416 of 2 mm in diameter and 10 cm in length, but diameters ranging from 0.5 to 5 mm and lengths ranging from 2 to 20 cm are industrially available and could be used. One or several lens(es), for example a GRIN lens 417 with pitch=0.5*n, n being a positive integer, typically pitch=0.5 or 1, can be attached to the GRIN relay lens, using for example glue. The length of said GRIN lens 417 is equal to the sum of the lengths of GRIN lenses 405 and 406 in the processing interferometer so as to compensate for the large path length difference and the dispersion. Said GRIN lens 417 is not required to be at the tip of the probe, it can also for example be placed before the detector. The reflectivity of the bond between the GRIN relay lens 416 and the GRIN lens 417 or the reflectivity of the surface of the GRIN relay lens 416, which constitutes the reference of the distal interferometer, can be adjusted in order to adjust the SNR of the set-up. The probe is placed in the proximity of the sample 418.

A beam splitter 415, for example a pellicle beam splitter, reflects light coming back from the probe through a focusing lens 419 onto the 2D detector 420, for example a CCD or CMOS camera. Two polarizers 421 and 422 and a quarter-wave plate 423 can be used in order to eliminate parasitic light. The beam splitter 415 and the two polarizers 421 and 422 can be replaced by a polarizing beam splitter cube.

Figure 8:
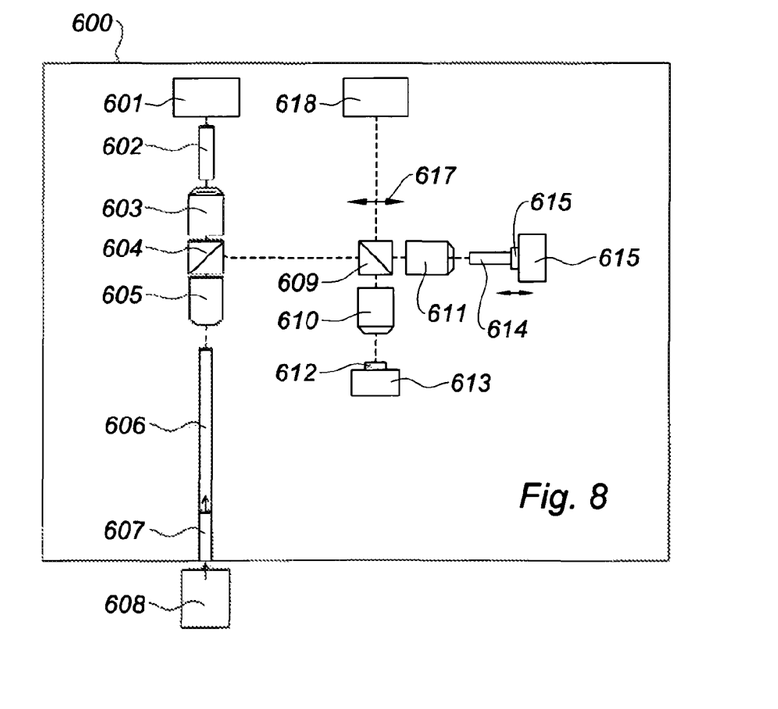
FIG. 8 shows an experimental set-up according to a fourth embodiment of a FF-OCT system with probe according to the invention.

FIG. 8 shows one embodiment of a FF-OCT set-up according to the invention, using a first lens based interferometer, a fiber bundle based probe, a second Linnik interferometer.

The FF-OCT set-up 600 comprises a light source 601, a beamsplitter 604, a fiber bundle 606 with one or several lens(es) 607 attached, a Linnik interferometer, a 2D detector 618.

The light source 601 is spatially and temporally incoherent in order to reduce crosstalks and consequently increase SNR. It can be for example a Xenon arc lamp. The emitted light is transported using for example an optical fiber 602 and a microscope objective 603.

Light is injected into the probe using for example a microscope objective 605. The probe can comprise a flexible fiber bundle 606, for example a bundle of 30 000 fibers for a diameter of 0.9 mm but other diameters ranging from 0.2 mm to a few mm are available and the number of fibers could be as large as 100 000 (see for example Sumitomo IGN-08/30 or Fujikura FIGH-100-1500N). One or several lens(es), for example a GRIN lens 607 with pitch=0.5*n, n being an integer, for example pitch=1, is attached to the fiber bundle 317 using for example optical glue. The reflectivity of the bond between the fiber bundle 606 and the GRIN lens 607 or the reflectivity of the surface of the fiber bundle 606, which constitutes the reference of the first interferometer, can be adjusted in order to adjust the SNR of the set-up. The probe is placed in the proximity of the sample 608.

A beamsplitter 604, for example a pellicle beamsplitter, reflects light coming back from the probe to a second interferometer. The second Linnik interferometer comprises a beamsplitter 609, for example a non-polarizing beamsplitter cube with anti-reflection coating, two microscope objectives with the same optical characteristics 610 and 611, two mirrors with the same optical characteristics 612 and 615, one or several lens(es), for example a GRIN lens 614 with same characteristics as the GRIN lens 607 used in the first interferometer, attached to one mirror in one arm, a motorized linear stage or actuator 613 for path length difference scanning, and a PZT actuator 615 used both for path length modulation and fine path length difference adjustments between the two arms.

Light coming from the second interferometer is focused on a 2D detector 618, for example a CCD or CMOS camera, using a focusing lens 617.

Contrary to the prior art, the embodiments described above enable a high SNR ensured by the use of light which exhibits both temporal and spatial incoherence in order to reduce crosstalks, by the use of polarizing optical elements which suppress the residual incoherent signal made by parasitic light, and by the use of a processing interferometer with large path length differences as explained before.

The system according to the invention can be used for, but not limited to endoscopic applications, medical and biomedical applications, non destructive control applications. It can also be coupled with other probes or endoscopes such as, for example, ultrasound probes.

In the medical or biomedical domain the use of the probe as or in an endoscope for imaging is a major application of one embodiment of the invention, in which the probe comprises a flexible fiber bundle. Its small diameter, typically 1 mm but other diameters from 0.2 to a few mm are possible given the wide range of industrially available bundles and lenses, makes it possible to insert it in the working channel of most existing medical endoscopes. It can be used by physicians for imaging of all internal organs or zones, for example but not limited to, the upper and lower gastrointestinal tracts, the pulmonary tract, the veins and arteries, the heart, the brain, the liver, the kidneys, the bladder, the prostate, etc. It can also be used by physicians or researchers for imaging of animals.

In the medical or biomedical domain the invention can also be used for imaging without the use of an endoscope, the probe being used as a hand-held needle-like probe, either rigid or flexible. In this configuration it can image organs like the upper gastrointestinal tract, the brain, the skin, the gynecological cavities, etc, on humans or animals. It can also be used during surgical operations, when one or several parts of the patient are opened, for imaging of accessible organs, for example the heart during a heart operation.

Of course, the invention is not restricted to the embodiments described above by way of non-limiting examples, but on the contrary it encompasses all embodiments thereof.

What is claimed is:

1. A full-field optical coherence tomography system for imaging an object, comprising:
   a light source generating an input light beam having a low temporal coherence;
   a processing interferometric device comprising:
      means for splitting the input light beam into a first input beam and a second input beam, the first input beam and the second input beam being recombined into a spectrally modulated output beam; and at least one reflecting surface of the processing interferometric device arranged to reflect the first input beam or the second input beam;
an imaging interferometric device comprising:
means for splitting the spectrally modulated output beam into a first output beam and a second output beam; and
at least one reflecting surface of the imaging interferometric device arranged to reflect the first output beam or the second output beam; and
a multichannel acquisition device arranged to receive a recombination of the first output beam and the second output beam, wherein the processing interferometric device includes at least one focusing optical element arranged between the means for splitting the input light beam and the at least one reflecting surface of the processing interferometric device, the at least one focusing optical element configured to focus at least one of the input beams onto the corresponding reflecting surface of the processing interferometric device,
wherein the at least one focusing optical element comprises at least one first lens, and a material of said first lens of the processing interferometric device induces an optical path length difference between the first and the second input beams of the processing interferometric device, said optical path length difference being compensated by a second lens, and
wherein the full-field optical coherence tomography system further comprises a probe coupled to the imaging interferometric device, said probe having a distal end to be placed in a proximity of the object and said second lens being placed at said distal end.

2. The full-field optical coherence tomography system according to claim 1, wherein the processing interferometric device has a first arm and a second arm respectively comprising a first reflecting surface and a second reflecting surface respectively arranged to reflect the first input beam and the second input beam, and wherein the at least one focusing optical element in said first arm or in said second arm respectively is arranged to focus the first input beam onto said first reflecting surface or the second input beam onto said second reflecting surface.

3. The full-field optical coherence tomography system according to claim 1, wherein the imaging interferometric device has a first arm and a second arm respectively comprising a first reflecting surface and a second reflecting surface respectively arranged to reflect the first output beam and the second output beam.

4. The full-field optical coherence tomography system according to claim 1, wherein said path length difference is substantially equal to an optical path length difference between the first beam and second beam of the imaging interferometric device.

5. The full-field optical coherence tomography system according to claim 1, wherein the at least one focusing optical element comprises objective optics so that the processing interferometric device forms a Linnik interferometer.

6. The full-field optical coherence tomography system according to claim 1, wherein said at least one first lens of the processing interferometric device and said second lens of the imaging interferometric device have same optical characteristics.

7. The full-field optical coherence tomography system according to claim 6, further comprising said probe is a miniaturized probe.

8. The full-field optical coherence tomography system according to claim 7, wherein the processing interferometric device or the imaging interferometric device presents a common optical path within the probe.

9. The full-field optical coherence tomography system according to claim 7, wherein the miniaturized probe comprises a fiber bundle having a diameter between about 0.2 mm and about 10 mm.

10. The full-field optical coherence tomography system according to claim 1, wherein at least two first lenses of the processing interferometric device are arranged to form an optical cavity, and at least two second lenses of the imaging interferometric device are arranged to form an optical cavity.

11. The full-field optical coherence tomography system according to claim 1, wherein said probe's distal end is oriented toward the object.

12. The full-field optical coherence tomography system according to claim 11, wherein the probe is a miniaturized probe comprising a plurality of optical lenses, each optical lens having a diameter between about 0.5 mm and about 5 mm.

13. The full-field optical coherence tomography system according to claim 1, wherein the optical path length difference is greater than or equal to about 1 mm.

14. The full-field optical coherence tomography system according to claim 1, wherein the full-field optical coherence tomography system comprises at least one polarizing optic arranged before the multichannel acquisition device.

15. The full-field optical coherence tomography system according to claim 1, further comprising at least one motorized component, the motorized component controlling the optical path length difference between the first input beam and the second input beam.

16. The full-field optical coherence tomography system according to claim 15, wherein the motorized component is arranged in the processing interferometric device or in the imaging interferometric device.

17. The full-field optical coherence tomography system according to claim 1, wherein said at least one first and second lenses are gradient index lens.

18. A full-field optical coherence tomography system for imaging an object, comprising:
a light source generating an input light beam having a low temporal coherence;
an imaging interferometric device comprising:
means for splitting the input light beam into a first input beam and a second input beam, the first input beam and the second input beam being recombined into a spectrally modulated output beam; and
at least one reflecting surface of the imaging interferometric device arranged to reflect the first input beam or the second input beam;
a processing interferometric device comprising:
means for splitting the spectrally modulated output beam into a first output beam and a second output beam;
at least one reflecting surface of the processing interferometric device arranged to reflect the first output beam or the second output beam; and
a multichannel acquisition device arranged to receive a recombination of the first output beam and the second output beam, wherein the processing interferometric device includes at least one focusing optical element arranged between the means for splitting the output light beam and the at least one reflecting surface of the processing interferometric device, the at least one focusing optical element configured to focus at least one of the output beams onto the corresponding reflecting surface of the processing interferometric device, wherein the at least one focusing element comprises at least one first lens, and a material of said first lens of the processing interferometric device induces an optical path length difference between the first and the second output beams of the processing interferometric device, said optical path length difference being compensated by at least one second lens, and wherein the full-field optical coherence tomography system further comprises a probe coupled to the imaging interferometric device, said probe having a distal end to be placed in a proximity of the object and said at least one second lens being placed at said distal end.

19. The full-field optical coherence tomography system according to claim 18, wherein said at least one first and second lenses are gradient index lens.

20. The full-field optical coherence tomography system according to claim 18, further comprising at least one motorized component, the motorized component controlling the optical path length difference between the first and the second output beams.

* * * * *